United States Patent [19]

Steiner et al.

[11] Patent Number: 5,152,745
[45] Date of Patent: Oct. 6, 1992

[54] INSUFFLATOR

[76] Inventors: Rolf Steiner, Schietingerstr.-22, 7270 Nagold-Gundringen; Volker Walz, Walddorferstr. 40, 7271 Rohrdorf, both of Fed. Rep. of Germany

[21] Appl. No.: 567,917

[22] Filed: Aug. 15, 1990

[30] Foreign Application Priority Data

Jun. 15, 1990 [DE] Fed. Rep. of Germany ....... 4019239

[51] Int. Cl.$^5$ ............................................. A61M 13/00
[52] U.S. Cl. ........................................ 604/26; 604/23; 128/747; 141/83; 141/197
[58] Field of Search ....................... 604/4, 23-31; 128/747, 748; 141/83, 94, 95, 197

[56] References Cited

U.S. PATENT DOCUMENTS

| | | | |
|---|---|---|---|
| 3,870,072 | 3/1975 | Lindemann | 604/26 |
| 4,527,600 | 7/1985 | Fisher et al. | 141/94 |
| 4,676,774 | 6/1987 | Semm et al. | 128/747 |
| 4,874,362 | 10/1989 | Wiest et al. | 128/747 |
| 4,966,578 | 10/1990 | Baier et al. | 604/26 |
| 5,006,109 | 4/1991 | Douglas et al. | 604/26 |
| 5,006,997 | 4/1991 | Reich | 604/31 |
| 5,013,294 | 5/1991 | Baier | 128/747 |
| 5,098,375 | 3/1992 | Baier | 604/23 |

Primary Examiner—Stephen C. Pellegrino
Assistant Examiner—Ralph A. Lewis

[57] ABSTRACT

By means of the invention, the pressure in a cavity can be measured, without ever reducing the gas flow to zero. This is achieved by bleeding an intermediate vessel slightly with its inlet valve closed and its outlet valve open and then being able to extrapolate from the pressure decrease whether the desired pressure has been reached. If the result of the extrapolation indicates that the desired pressure has not been reached, then pumping is repeated, measuring is repeated and so on and so forth until the extrapolation indicates that the desired pressure has been reached. Thus extrapolations are made instead of allowing the intermediate vessel to empty completely.

11 Claims, 4 Drawing Sheets (1) $P_2 = \dfrac{P_b - P_a \times x}{1 - x}$ (2) $x = -0.5 \times \dfrac{(P_c - P_a)}{(P_a - P_b)} - \sqrt{\left[\dfrac{(P_c - P_b)}{(P_a - P_b)} + \dfrac{1}{4} \times \left[\dfrac{(P_c - P_a)}{(P_a - P_b)}\right]^2\right]}$ (3) $x = \dfrac{P_b - P_c}{P_a - P_b}$ (4) $R = \dfrac{-t_1}{V \times \ln(x)}$ (5) $F = \dfrac{P_v - P_l}{P_u} \times V$

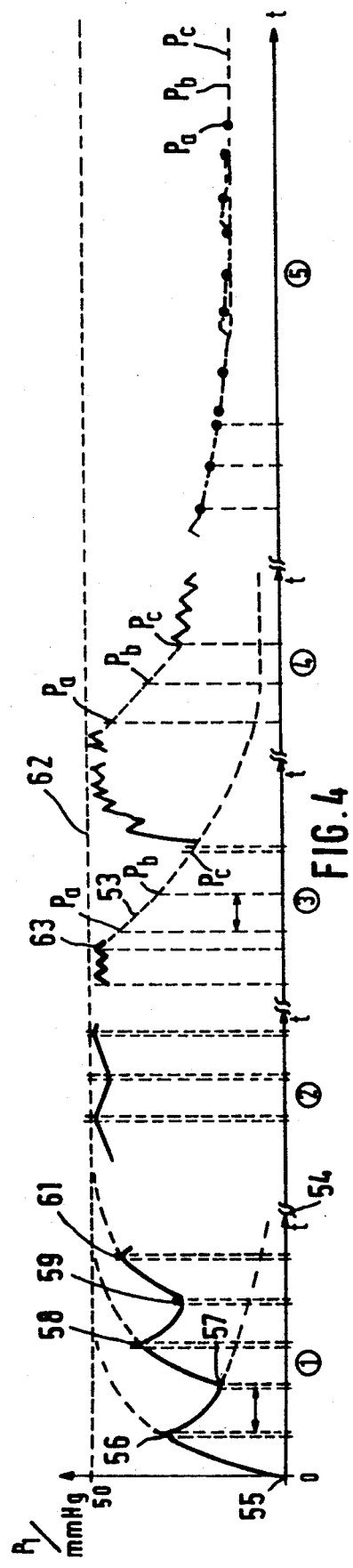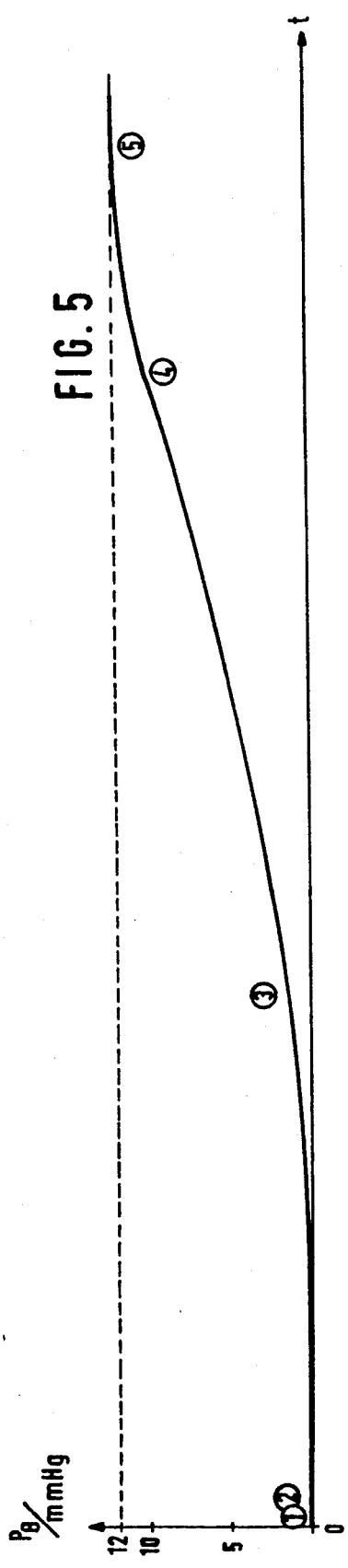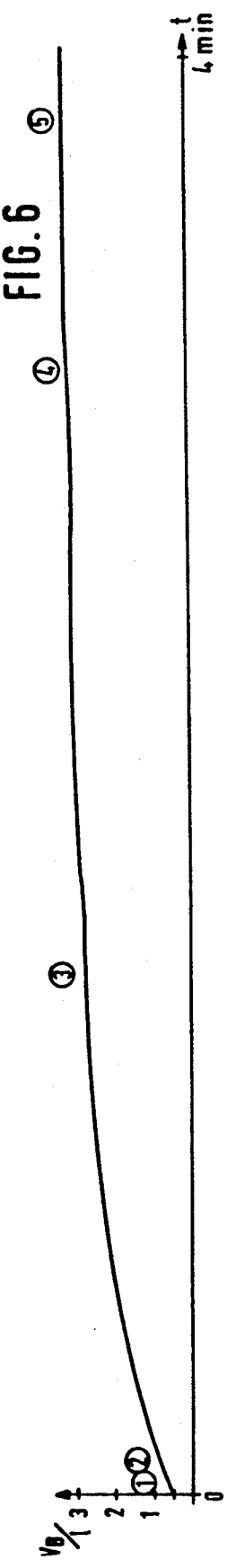
FIG. 4
FIG. 5
FIG. 6

INSUFFLATOR

The invention relates to an insufflator by means of which the pressure of a fluid insufflated into a body cavity can be measured and controlled.

BACKGROUND OF THE INVENTION

Such a device is known for German Patent Specification 3,000,218, which corresponds to U.S. Pat. No. 4,464,169. Such body cavities are, above all, cavities in the body of humans and animals, especially the abdominal cavity. But body cavities are also regions which are not cavities per se, such as the gap in the knee joint which can be widened to form a body cavity by pumping it up.

Devices of the known type require a large number of components and measuring element. Moreover, in all the instruments, the measurement of the pressure in the body cavity is carried out in such a way that the gas through-flow is reduced to zero. The maximum obtainable throughflow is thus restricted considerably. Furthermore, the gas throughflow has an appreciable pulsation.

SUMMARY OF THE INVENTION

The object of the invention is to provide a means by which, during the measurement of the pressure in the cavity, there is no need to reduce the throughflow of the fluid to a zero value or virtually to a zero value.

According to the invention, this object is achieved by means of an insufflator having the following structural features:

an inlet line, a first valve device following said inlet line, a second valve device provided downstream of said first valve device, an intermediate vessel for said fluid provided between said first and said second valve devices, an outlet line downstream of said first valve device and said intermediate vessel a logic device adapted to calculate the pressure of said fluid in said body cavity from at least two falling pressures of said intermediate vessel that occur successively in time and to control said first and second valve devices, a pressure indicator controlled by said logic device for indicating the pressure of said fluid in said body cavity, and a pressure/voltage converter connected between said intermediate vessel and said logic device.

When the second valve device is opened, the pressure in the intermediate vessel decreases according to specific regularity. If the conditions were ideal, including a constant flow resistant, then the pressure in the intermediate vessel would decrease exactly according to an e-function. If two values of an e-function and its decrease constant Tau are known, its trend can be determined. In particular, it is possible to determine the particular lowest value which it approaches asymptotically. The asymptotic value is equal to the pressure in the cavity.

The decrease constant Tau is calculated from the resistance * intermediate vessel volume. However, for various reasons the resistance is not constant. For example, different hollow needles are used at the end of the outlet line and themselves have a differing resistance. Depending on the site of the outlet line, which is flexible in the end region, its resistance too varies. It can also happen that the hollow needle assumes differing narrowing of its cross-section from the outset or during its use. Finally, resistance is also of differing amount as a result of turbulences. For example, it can be greater at a higher pressure than at low pressure and so on and so forth.

Since the decrease constant Tau is therefore not known or is known only inexactly, in practice three (or more) measuring points are required.

The asymptote can be calculated from these. If the precalculated asymptotic curve is below the desired pressure in the cavity, further pumping must be carried out until the asymptote corresponds to the desired pressure.

The logic device can consist of a microprocessor, the programming of which does not constitute an inventive step and for which this is easily possible. It is not fully loaded by computing and control tasks of this type even when the simplest type of microprocessor is used.

The described embodiments include the following additional advantageous features.

The first valve device is a CLOSED-OPEN valve device. By this means, simple conditions are obtained at the inlet, it can be cheap and there is no problem in improving the fluid throughflow by means of a plurality of parallel branches.

The second valve device is a CLOSED-OPEN valve device. The same is true according to this feature.

For holding gaseous fluids, the intermediate vessel is rigid. As a result, the intermediate vessel has a constant volume, this making the computations easier.

For holding incompressible fluids, the intermediate vessel has a specific elasticity. By these features it would be possible also to use incompressible fluids, and the necessary computations can nevertheless still be executed reliably.

The input line leads to a branching point. At least two branches, each including first and second valve devices and an intermediate vessel are arranged parallel to one another and merge via a junction point into the outlet line. And the first and second valve devices in said branches are connected to the logic device and are activatable in a manner offset in time periods. This gives rise to an especially practicable form. Even large body cavities, such as, for example, a human abdomen, can then be inflated reasonably quickly. However, where body cavities of large animals, such as, for example, elephants, are concerned, it is advisable to provide a larger number of branches.

In these instances too, the throughflow quantity can be calculated by means of a plurality of pressure/voltage converters that connect the intermediate vessels in the branches to the logic device.

The first and second valve devices are CLOSED-OPEN valve devices having variable CLOSED-OPEN times. As a result this time can be adapted to the various working phases. For example, during the filling of he intermediate vessel, the valve device at the inlet can be set to "OPEN" for a longer time initially, as long as the intermediate vessel is not yet full, and this time can be reduced, the nearer the final pressure. Also, when the asymptote is to be calculated, it is possible to shorten or lengthen the measuring times which serve for computing the asymptotic curve of the e-function or of functions similar to the e-function.

The more filling cycles that are provided for the intermediate vessel, the greater the difference between the actually calculated pressure of said fluid in said body cavity and the desired pressure therein. This ensures that the desired pressure in the intermediate vessel can be approached as finely as possible. When the desired pressure is reached, the filling can then be cut off completely.

A fluid-quantity indicator is provided and is controlled by the logic device. This affords not only a pressure measurement, but also, without any further outlay in terms of equipment, a quantity measurement.

A buffer store is provided following the second valve device. By these means media flow in the hollow needle can be smoothed, so that a continuous flow is obtained.

The logic device is adapted not to open the first and second valve devices simultaneously.

BRIEF DESCRIPTION OF THE DRAWINGS

The invention is now described by reference to preferred exemplary embodiments.

In the drawing.

FIG. 4 shows a pressure/time diagram for the intermediate vessel 23.

FIG. 5 shows a time diagram of the pressure in the abdomen.

FIG. 6 shows a time diagram of the flowed gas volume.

DESCRIPTION OF PREFERRED EMBODIMENTS

Figure 1:
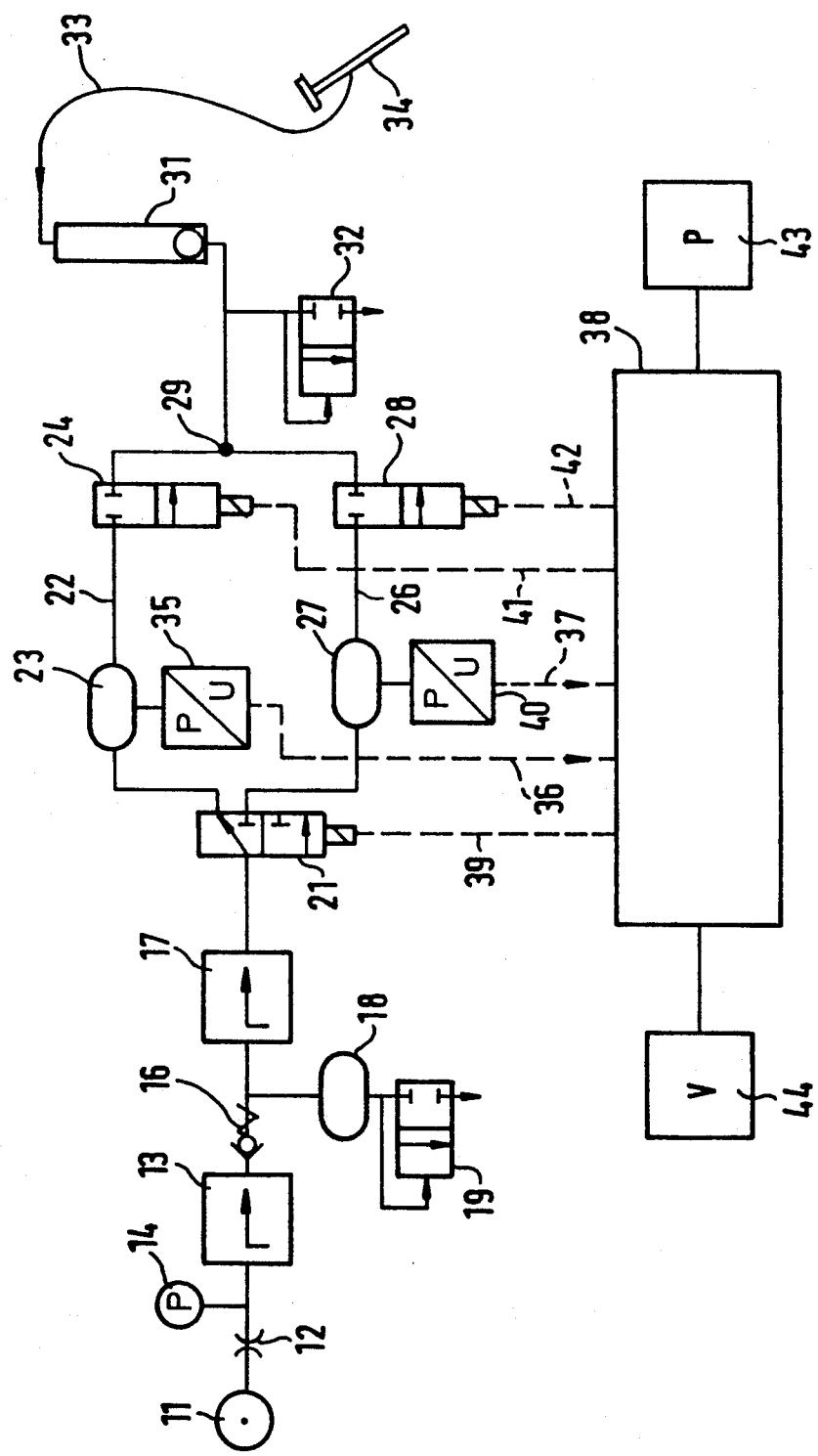
FIG. 1 shows a block diagram of a first embodiment.

According to FIG. 1, a gas bottle 11 is followed by a shutoff cock 12. This is connected to a pressure reducer 13. A gas-quantity supply indicator 14 branches off between these two. The pressure reducer 13 is followed by a nonreturn valve 16. While the pressure reducer 13 reduces the pressure to a few bar (for example 4), a pressure reducer 17 lowers this pressure to 50 mm Hg. An intermediate vessel 18 branches off between 16 and 17 and is itself connected to a relief valve 19. If 13 fails, then 19 blows off excess pressure. 17 is connected to a shuttle valve 21 which has one inlet and two outlets. However, depending on the position of the valve, gas is conveyed through only by way of one outlet or the other.

A second intermediate vessel 23 is located in a first branch 22 after the upper outlet of 21 and is followed by an outlet valve 24 which has a CLOSED position and an OPEN position. Parallel to this and of an exactly identical design is a second branch 26 with an intermediate vessel 27 and an outlet valve 28. The intermediate vessels 23, 27 are rigid and have a content of, for example 0.25 liters. The outlet of 24, 28 leads to a junction point 29 leading to a gas meter 31. It can be seen from this whether any gas at all is flowing. This is not a through-flow meter. A relief valve 32 branches off between 29 and 31, serves for safety purposes and prevents the possibility that the pressure in the body cavity will rise above a particular value. 31 is followed by a flexible hose 33, and to this is connected a hollow needle 34.

A converter 35, 40 is connected both to 23 and to 27 and converts the pressure prevailing in 23, 27 into a voltage. These voltages are fed to a control 38 via electrical lines 36, 37. The control 38 sets the shuttle valve 21 and the outlet valves 24, 28 into one of their positions or the other via electrical lines 39, 41 and 42. If 21 is OPEN for the branch 22, then 24 is CLOSED. It is also true of 22 that, when 24 is OPEN, 21 is CLOSED for 22. The same applies accordingly to the branch 26. In the control 38 there is a microprocessor with functions to be explained later.

A buffer vessel 70 can be provided after the junction point 29.

The control 38 controls a pressure indicator 43 and a volume indicator 44. The block diagram according to FIG. 2 again shows a large number of components. Differences are that the nonreturn valve 16 is omitted. Also, there is no intermediate vessel 18, the purpose of which is to allow a gas bottle to be changed without interrupting the operation of the device. There is also no gas meter 31, and instead of the relatively expensive relief vale 32 there is, here, an overpressure switch 46 which interrupts the gas flow to the hollow needle in the event of excess pressure and which, for example does not bleed off pressure in the same way as the relief valve 32.

Figure 2:
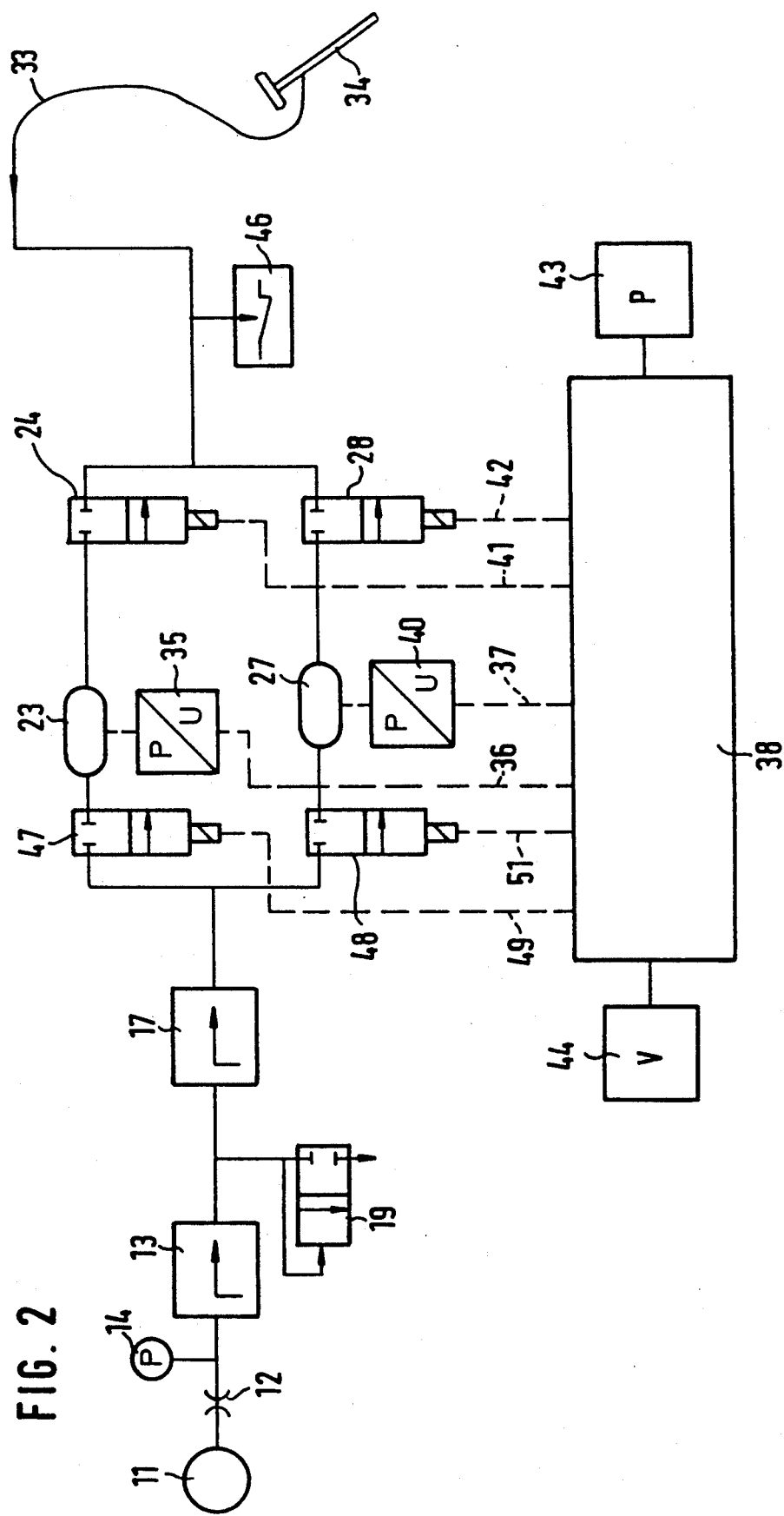
FIG. 2 shows a block diagram of a second embodiment.

Above all, in the second exemplary embodiment, there are instead of the shuttle valve 21 two inlet valves 47, 48 which have only one OPEN and the CLOSED position and which are set in their position by the control 38 via electrical lines 49, 51. There are therefore inlet and outlet valves of identical design here, thus improving the response behavior, price or the like. In FIG. 2, like parts are designated by the same reference symbol as in FIG. 1.

It is assumed (FIG. 3) that the intermediate vessel 23 has been pumped up to a pressure 50 mm Hg, 24 being closed (FIG. 2) and 47 being open. By means of 38 the inlet valve 47 is now closed and 24 opened. This takes place at the time 52.

Figure 3:
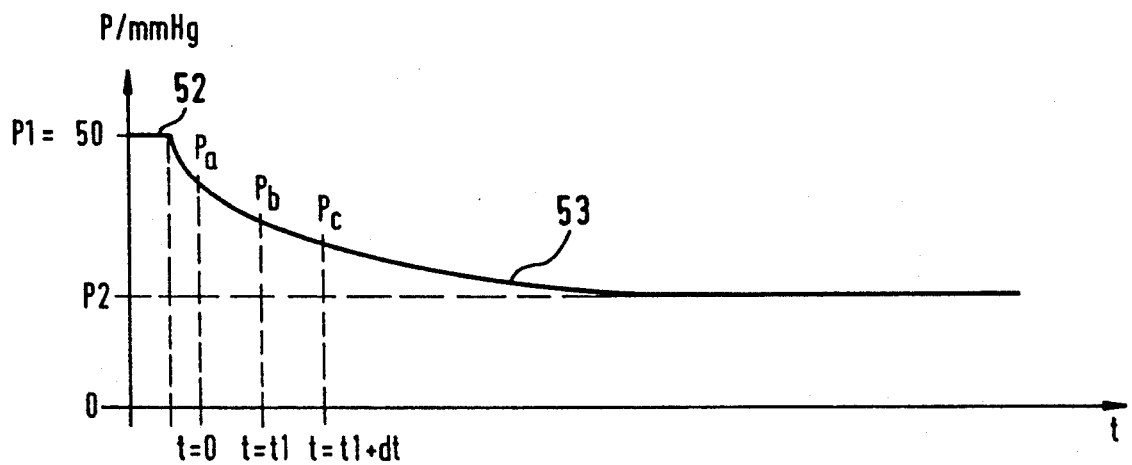
FIG. 3 shows a representation of a fall-off curve together with formula for computing the relevant variables.

Gas now flows via 34 into the abdomen (not shown) and the pressure in 23 falls according to the curve 53. However, in the actual situation the outlet valve 24 is closed again after the measurement of Pc. But if it continues to remain open, the pressure would fall further, as shown in FIG. 3. In a first cycle, P2 is on the t-axis, and the more volume passes out of 23 into the abdomen, the higher P2 becomes. The line passing through P2 and parallel to the t-axis can be considered as an asymptote.

The pressure is now measured, in the exemplary embodiment at intervals of 100 msec. at the time t=0, the time t=t1 and the time t=t1+dt, the time intervals all being equal. The control 38 learns of the falling pressure $P_a$, $P_b$ and $P_c$ via the line 36. According to FIG. 3, the pressure $P_2$ is obtained by formula (1). Formula (2) indicates the value for x. Formula (3) is equivalent to formula (2). Since the desired pressure in the abdomen has previously been set at the control 38, the control 38 can determine whether this has been reached or not reached by P2. The necessary computing and comparing work can be carried out by the simplest microprocessor, without it being overloaded. The programming too per se does not itself present any difficulties.

The resistance can also be calculated according to the formula (4), V being the volume of intermediate vessel 23.

The gas quantity which as flowed through can be calculated by means of the formula (5). In this, Pv is the pressure in the filled intermediate vessel (FIG. 4, Nos. 56, 58, 61), P1 is the pressure in the (partially) emptied intermediate vessel (FIG. 4, Nos. 57 and 59), Pu is the ambient pressure and V is once again the volume of the intermediate vessel.

FIG. 6 shows that after four minutes the gas volume in the patient remains constant at somewhat more than three liters. To have a measure of the approximate gas quantity absorbed by the patient, a measurement of the throughflow quantity is important.

FIG. 5 has the same time scale as FIG. 6. It can be seen, here, how the pressure in the abdomen approaches approximately 12 mm Hg.

FIG. 4 which is of most interest doe snot have the same time scale as FIGS. 5 and 6. On the contrary, here the time segments 1, 2, 3, 4, 5, each surrounded by a circle, have been shown enlarged and the time axis has been broken at a respective interruption 54. In the period 1, at the point 55 the outlet valve 24 is closed and the inlet valve 47 opened. After 110 msec, at the point 56, 47 is now closed and 24 opened and the pressure in 23 measured. Gas now flows into the abdomen. After the same time, namely after 110 msec, at the point 57 a measurement is made again, 24 is closed and 47 is opened. The pressure now rises in 23. At the point 58, 47 is closed and 24 opened, and the pressure falls. The same occurs at point 59 as at point 578 and the same at point 61 as at point 58. The peak points come increasingly closer to the 50 mm Hg line 62. The time interval for the measurement and changeover, is always the same, namely 110 msec. In the timer period 2, the valleys have become very shallow. After the point 63, the intermediate vessel 23 is no longer pumped up, but is now emptied only along the curve 53. At intervals of 100 msec, $P_a$, $P_b$ and $P_c$ are measured, and the control 38 draws the abovementioned conclusions. After the measurements $P_c$, pumping is now carried out again, as previously described, virtually up to the 50 mm Hg line, and $P_a$, $P_b$ and $P_c$ are measured again. Of course, the cycles are substantially more numerous than as shown in FIG. 4 and this also emerges from a comparison with FIG. 5.

In the time segment 4, the intermediate vessel has to be pumped up only a few times. For example, in the time segment 1 the intermediate vessel 23 has to be connected to the pressure reducer 17 ten times, in time segment 4 only five times and in time segment 5 not at all. If $P_a$, $P_b$ and $P_c$ are measured in the time segment 5, it is ascertained that the desired pressure in the abdomen has been reached. How much gas must then still flow into the abdomen is determined solely by means of the gas absorption of the patient and a possible leak. Too much gas must not diffuse into the body, where a human or animal body is concerned, because otherwise too much gas of this kind passes into the blood. In the period 5, for long spells the intermediate vessel 23 is no longer charged at all or charged only very slightly, that is to say, in this time segment, there are long periods in which 47 remains closed and 24 open. During this time $P_2$ is measured statically.

This applies to the branch 22.

Exactly the same is true of the branch 26, but phase-shifted by half the measuring cycle. The same slope of FIG. 4 must therefore be imagined once again as being shifted by 55 msec. A smoothing effect with regard to the junction point 29 would thereby be obtained, and the remainder of the voltage unevenness can then be smoothed by means of the buffer vessel 70.

Where there are 3 branches, there are 3 slopes shifted respectively by a third of a period. More than one branch causes the curve to rise according to FIG. 5, so that the desired pressure is reached earlier, and this in turn means, according to FIG. 6, that the gas volume required is insufflated sooner.

We claim:

1. An insufflator by means of which the pressure of a fluid insufflated into a human or animal body cavity can be measured and controlled, comprising:
    an inlet line,
    a first valve device following said inlet line,
    a second valve device provided downstream of said first valve device,
    said second valve device following said inlet line,
    a second valve device provided downstream of said first valve device,
    said second valve device being a CLOSED-OPEN device having variable CLOSED-OPEN times,
    an intermediate vessel for said fluid provided between said first and said second valve devices,
    an outlet line downstream of said first valve device, said second valve device and said intermediate vessel,
    conduit means for conveying fluid between said inlet line and said first valve device and between said first valve device and said intermediate vessel and between said intermediate vessel and said second valve device and between said second valve device and said outlet line,
    a logic device,
    a pressure/voltage converter connected between said intermediate vessel and said logic device for applying signals to said logic device corresponding to falling pressures in said intermediate vessel,
    said logic devices being comprised of means for registering the values of said signals and means for calculating the pressure of said fluid in said body cavity as a function of signals corresponding to at least two falling pressures in said intermediate vessel that occur successively in time,
    said logic device being arranged to control said first valve device and said second valve device, and
    a pressure indicator controlled by said logic device for indicating the pressure of said fluid in said body cavity.

2. An insufflator as claimed in claim 1, wherein said first valve device is a CLOSED-OPEN valve device.

3. An insufflator as claimed in claim 1, wherein, for holding gaseous fluids, said intermediate vessel is rigid.

4. An insufflator as claimed in claim 1, wherein said input line leads to a branching point, at least two branches, each of which includes first and second valve devices and an intermediate vessel, are arranged parallel to one another and merge via a junction point into said outlet line, and said first and second valve devices in each of said branches are connected to said logic device and are activatable in a manner offset in time periods.

5. An insufflator as claimed in claim 4, wherein a plurality of pressure/voltage converters connect said intermediate vessels in said branches of said logic device.

6. An insufflator as claimed in claim 1, wherein said first valve device is a CLOSED-OPEN valve device having variable CLOSED-OPEN times.

7. An insufflator as claimed in claim 1 or 6, wherein said logic device is comprised of means for calculating the pressure of fluid in said body cavity as a function of signals corresponding to the fall in pressure in said intermediate vessel whereby the more filling cycles that are provided for said intermediate vessel, the greater the difference between the actually calculated pressure of said fluid in said body cavity and desired pressure therein.

8. An insufflator as claimed in claim 1, further comprising a fluid-quantity indicator controlled by said logic device.

9. An insufflator as claimed in claim 1, further comprising a buffer vessel following said second valve device.

10. An insufflator as claimed in claim 1, wherein said logic device is comprised of means for preventing opening of said first and second valve devices simultaneously.

11. An insufflator as claimed in claim 1, wherein said intermediate vessel has a defined module of elasticity that is effective for holding incompressible fluids in the pressure range used in said conduit means downstream of said first valve device.

* * * * *